(12) United States Patent
Williamson, IV et al.

(10) Patent No.: US 7,905,842 B2
(45) Date of Patent: Mar. 15, 2011

(54) APPARATUS AND METHOD FOR EXCISING TISSUE AND BANDAGING THE RESULTING WOUND

(75) Inventors: Warren P. Williamson, IV, Loveland, OH (US); Michael K. Banbury, Rockland, DE (US); Jillian E. Banbury, Rockland, DE (US)

(73) Assignee: The Cleveland Clinic Foundation, Cleveland, OH (US)

( * ) Notice: Subject to any disclaimer, the term of this patent is extended or adjusted under 35 U.S.C. 154(b) by 667 days.

(21) Appl. No.: 11/639,098

(22) Filed: Dec. 14, 2006

(65) Prior Publication Data

US 2007/0142853 A1 Jun. 21, 2007

Related U.S. Application Data

(60) Provisional application No. 60/752,552, filed on Dec. 21, 2005.

(51) Int. Cl.
*A61B 10/00* (2006.01)

(52) U.S. Cl. ....................................................... 600/562

(58) Field of Classification Search .................. 600/562, 600/564; 602/41, 42, 43; 604/317; 607/96
See application file for complete search history.

(56) References Cited

U.S. PATENT DOCUMENTS

| | | | |
|---|---|---|---|
| 3,971,384 A | 7/1976 | Hasson | |
| 4,913,138 A | 4/1990 | Yoshida et al. | |
| 5,449,340 A | 9/1995 | Tollini | |
| 5,562,705 A | 10/1996 | Whiteford | |
| 6,225,522 B1 | 5/2001 | Schroeder | |
| 6,299,018 B1 * | 10/2001 | Kimbrell | 221/71 |
| 6,573,421 B1 | 6/2003 | Lemaire | |
| 6,685,682 B1 | 2/2004 | Heinecke et al. | |
| 7,210,609 B2 * | 5/2007 | Leiboff et al. | 227/180.1 |
| 2002/0064619 A1 | 5/2002 | Schroeder | |
| 2002/0107466 A1 | 8/2002 | Faasse, Jr. | |
| 2004/0186406 A1* | 9/2004 | Falahee | 602/57 |
| 2004/0215217 A1 | 10/2004 | Banbury et al. | |
| 2005/0184121 A1* | 8/2005 | Heinrich | 227/175.1 |
| 2005/0234485 A1 | 10/2005 | Seegert et al. | |
| 2005/0274453 A1* | 12/2005 | Anvar | 156/247 |

* cited by examiner

*Primary Examiner* — Max Hindenburg
*Assistant Examiner* — Fangemonique Smith
(74) *Attorney, Agent, or Firm* — Wood, Herron & Evans, L.L.P.

(57) ABSTRACT

An apparatus (10) and method for excising tissue (208) and closing a wound (156) that results from excision of the tissue (208) is provided. The apparatus (10) includes structure (14) defining an aperture (34) into which tissue (208) to be excised is exposed and a cutting member (96). The apparatus (10) also includes an adhesive bandage (140) for closing the wound (156). The adhesive bandage (140) is secured relative to a lower surface (20) of the structure (14) in a location for contacting skin (154) adjacent to the tissue (208) to be excised. The apparatus (10) further includes a device (150) that is actuatable for closing the wound (156) with the adhesive bandage (140) and actuators (108 and 182) for moving the cutting member (96) relative to the structure (14) for excising the tissue (208) exposed in the aperture (34) and for actuating the device (150).

14 Claims, 10 Drawing Sheets

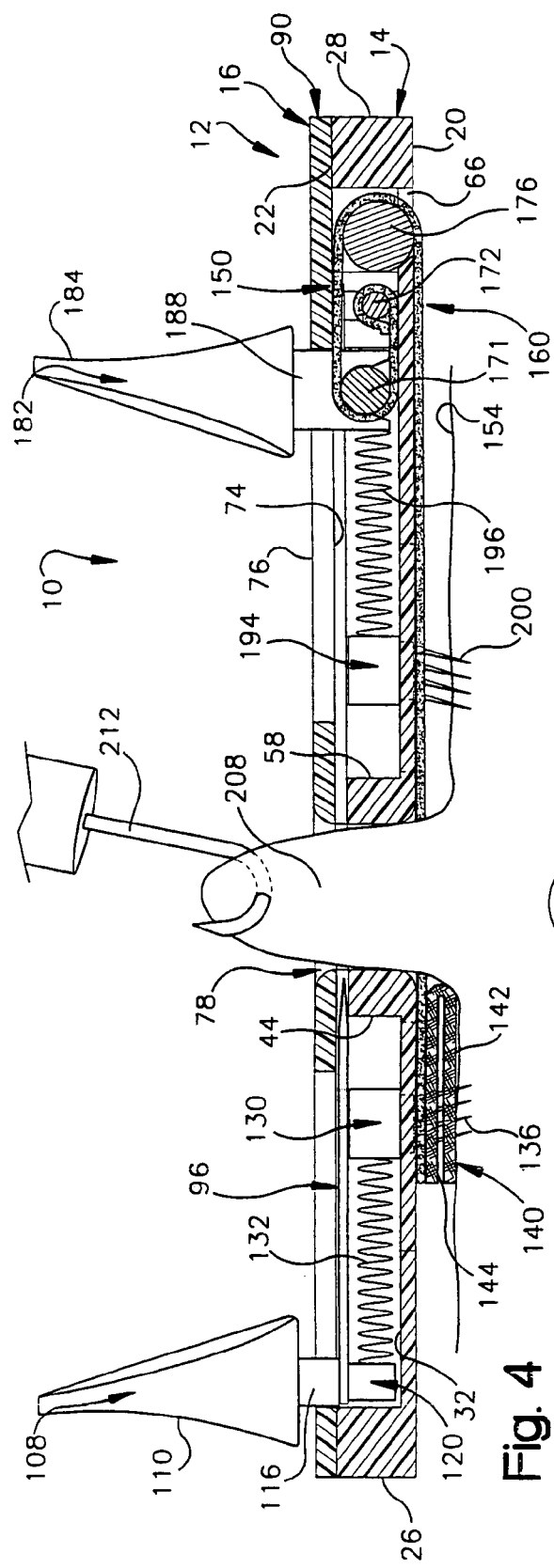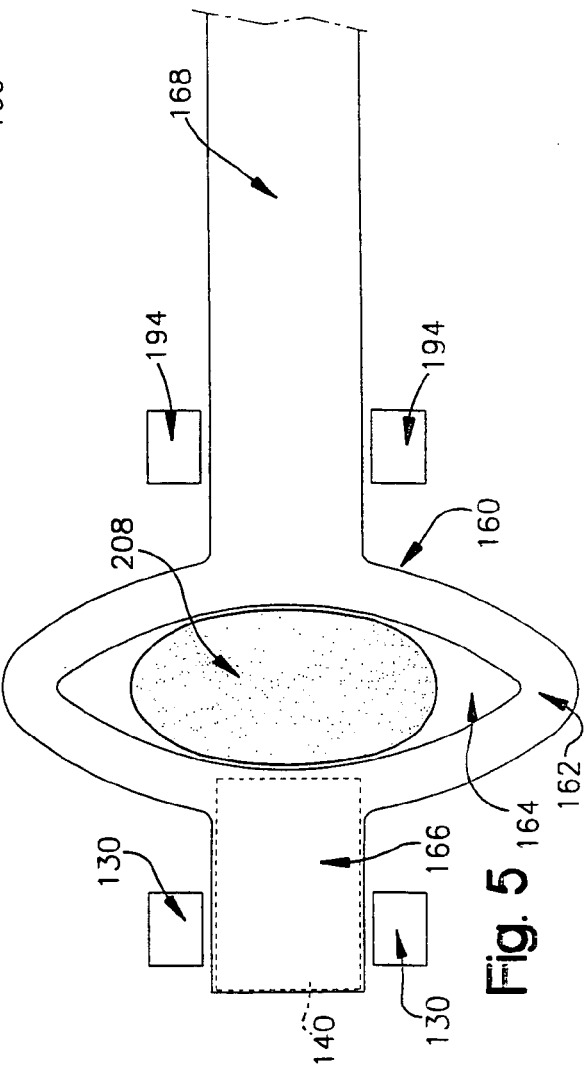
Fig. 4
Fig. 5

APPARATUS AND METHOD FOR EXCISING TISSUE AND BANDAGING THE RESULTING WOUND

RELATED APPLICATION

This application claims priority from U.S. Provisional Application No. 60/752,552, filed Dec. 21, 2005, the subject matter of which is incorporated herein by reference.

TECHNICAL FIELD

The present invention relates to an apparatus and method for excising tissue, such as skin lesions, and for closing a wound that results from excision of the tissue. More particularly, the present invention relates to an apparatus and method for excising tissue and closing a wound that results from excision of the tissue with an adhesive bandage.

BACKGROUND OF THE INVENTION

It is common practice for physicians, such as dermatologist, to excise small segments of tissue from a human. For example, lesions may be removed from the skin during a screening for skin cancer. Small segments of tissue may also be excised for cosmetic purposes, such as the removal of a mole.

A wound results from the excision of the tissue. It is desirable to close the resulting wound. Some physicians use a scalpel to excise the tissue. After the tissue is excised, the resulting wound is sutured closed.

U.S. patent application Ser. No. 10/845,313, published as U.S. Patent Application Publ. No. 2004/0215217 and which is assigned to the assignee of the present invention, discloses an apparatus for excising tissue and closing the resulting wound with a clip. The disclosed apparatus significantly reduces the time required for a physician to excise the tissue and close the resulting wound.

Some physicians prefer to close the wound resulting from the excision of tissue with an adhesive bandage. As a result, an apparatus for excising tissue and closing the resulting wound with an adhesive bandage is desirable.

SUMMARY OF THE INVENTION

The present invention relates to an apparatus for excising tissue and closing a wound that results from excision of the tissue. The apparatus comprises structure defining an aperture into which tissue to be excised is exposed. The apparatus also comprises a cutting member and an adhesive bandage for closing the wound. The adhesive bandage is secured relative to a lower surface of the structure in a location for contacting tissue adjacent to the tissue to be excised. A device of the apparatus is actuatable for closing the wound with the adhesive bandage. The apparatus further comprises actuators for moving the cutting member relative to the structure for excising the tissue exposed in the aperture and for actuating the device.

According to another aspect, the present invention relates to a method for excising tissue and closing a wound that results from excision of the tissue. The method comprises the steps of: contacting tissue adjacent to the tissue to be excised with an adhesive bandage that is secured relative to a lower surface of a structure; exposing the tissue to be excised into an aperture formed in the structure; moving a cutting member relative to the structure for excising the tissue that is exposed in the aperture; and actuating a device for closing the wound with the adhesive bandage.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 4 is a sectional view of the apparatus of FIG. 1 and illustrates the device in the initial position;

FIG. 5 schematically illustrates a condition of a liner of the apparatus when the device is in the initial position;

DETAILED DESCRIPTION OF THE INVENTION

Figure 1:
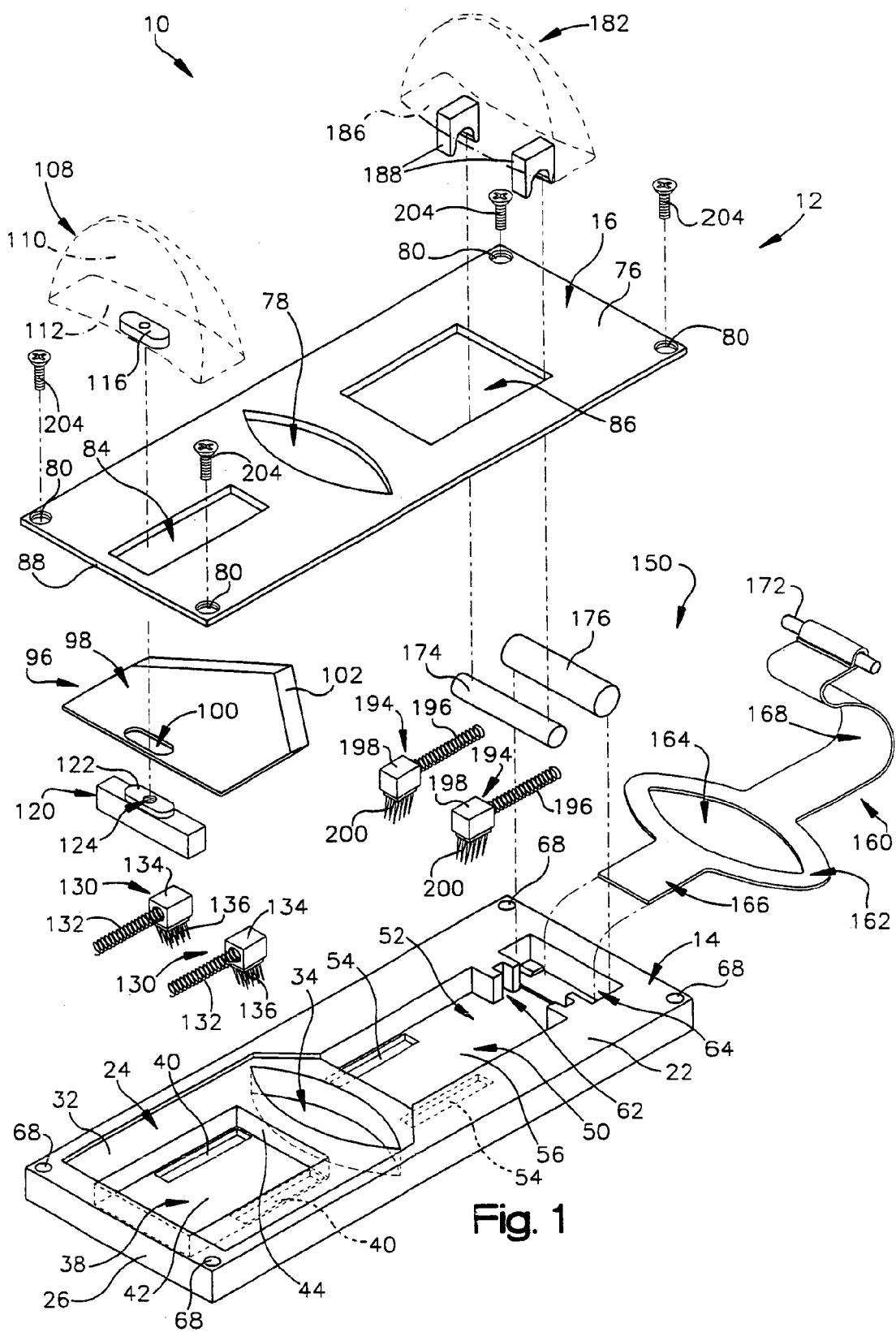
FIG. 1 is an exploded perspective view of an apparatus constructed in accordance with the present invention.
Figure 2:
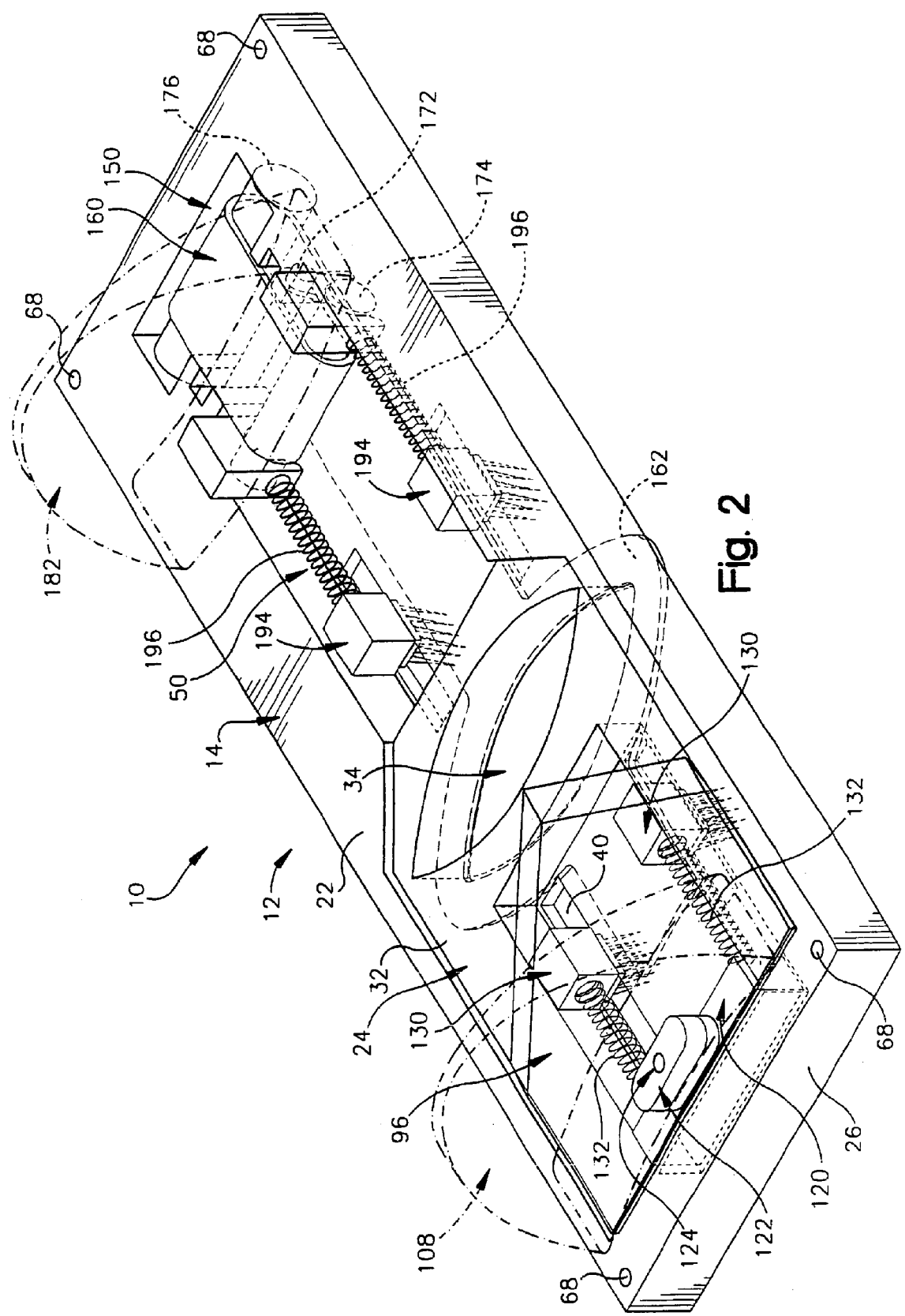
FIG. 2 is a perspective view of a portion of the apparatus of FIG. 1.

FIG. 1 is an exploded perspective view of an apparatus 10 constructed in accordance with the present invention. The apparatus 10 includes a housing 12 having a base plate portion 14 and a top plate portion 16.

The base plate portion 14 of the housing 12 is generally rectangular and includes lower and upper surfaces 20 and 22 (FIG. 4), respectively. As shown in FIG. 1, a shallow recess 24 extends into the upper surface 22 of the base plate portion 14. The recess 24 is located between a first end surface 26 of the base plate portion 14 and longitudinal mid-point of the base plate portion. The longitudinal mid-point is located approximately equidistance between the first end surface 26 and a second end surface 28 (FIG. 4) of the base plate portion 14. The recess 24 includes a bottom surface 32 that is oriented parallel to the lower and upper surfaces 20 and 22 of the base plate portion 14.

An elliptical aperture 34 extends through the base plate portion 14 from the lower surface 20 to the bottom surface 32 of the recess 24. The elliptical aperture 34 is located adjacent to the longitudinal mid-point of the base plate portion 14.

A rectangular recess 38 extends into the base plate portion 14 from the bottom surface 32 of the recess 24. Two longitudinally elongated slots 40 extend between a bottom surface 42 of the rectangular recess 38 and the lower surface 20 of the base plate portion 14. The longitudinally elongated slots 40 are laterally spaced from one another and, each slot 40 terminates adjacent a side wall 44 of the recess 38 located nearest the elliptical aperture 34.

With reference to FIG. 1, another recess 50 extends into the upper surface 22 of the base plate portion 14 between the longitudinal mid-point and the second end surface 28. The recess 50 extends into the base plate portion 14 a depth approximately equal to the depth of recess 38. The recess 50 includes a rectangular portion 52 that is located adjacent to the elliptical aperture 34. Two longitudinally elongated slots 54 extend between a bottom surface 56 of the rectangular portion 52 of the recess 50 and the lower surface 20 of the base plate portion 14. The longitudinally elongated slots 54 are laterally spaced from one another and, each slot 54 terminates adjacent a side wall 58 (FIG. 4) of the recess 50 located nearest the elliptical aperture 34. As shown in FIG. 1, the recess 50 also includes an anchor pin slot 62 and a roller slot 64. The roller slot 64 is located nearest the second end surface 28 of the base plate portion 14. A through-hole 66 (FIG. 4) extends through the base plate portion 14 between the roller slot 64 and the lower surface 20 of the base plate portion 14. The anchor pin slot 62 is located between the roller slot 64 and the rectangular portion 52 of the recess 50.

The base plate portion 14 also includes four fastener holes 68. The four fastener holes 68 extend into upper surface 22 of the base plate portion 14. One fastener hole 68 is located in each corner of the base plate portion 14.

The top plate portion 16 of the housing 12 also includes lower and upper surfaces 74 and 76 (FIG. 4), respectively. An elliptical aperture 78 extends through the top plate portion 16 of the housing 12 at a location corresponding to the elliptical aperture 34 of the base plate portion 14. As shown in FIG. 4, the upper surface 76 of the top plate portion 16 is chamfered adjacent the elliptical aperture 78. Four fastener holes 80 (FIG. 1) extend through top plate portion 16. Each of the four fastener holes 80 is associated with and has a location corresponding to a fastener hole 68 of the base plate portion 14 of the housing 12.

First and second rectangular openings 84 and 86, respectively, also extend through the top plate portion 16 of the housing 12. The first rectangular opening 84 is located between a first end surface 88 of the top plate portion 16 and the elliptical aperture 78. The first rectangular opening 84 extends longitudinally over a distance equal to the longitudinal distance of the recess 38 in the base plate portion 14 and extends laterally over a distance less than the lateral extent of the recess 38. The second rectangular opening 86 is located between the elliptical aperture 78 and a second end surface 90 (FIG. 4) of the top plate portion 16. The second rectangular opening 86 extends longitudinally over a distance equal to the rectangular portion 52 of the recess 50 and extends laterally over a distance slightly less than the lateral extent of the rectangular portion 52.

The apparatus 10 also includes a cutting member or blade 96. The blade 96 includes a main body portion 98 through which an oval aperture 100 extends. The blade 96 also includes a sharpened edge 102. The blade 96 is formed from surgical steel. In one embodiment of the invention, the blade 96 is formed from 440 stainless steel.

An actuator handle 108 of the apparatus 10 is molded from plastic and includes an actuation surface 110 and a rectangular lower surface 112. A projection 116 extends below the lower surface 112 of the actuator handle 108. The projection 116 is sized for being received in the first rectangular opening 84 of the top plate portion 16 of the housing 12. A locking pin (not shown) extends downwardly from the projection 116.

An actuator block 120 is located beneath the blade 96. The actuator block 120 is a parallelepiped. An oval boss 122 extends upwardly from the actuator block 120. The oval boss 122 is sized for fitting snugly in the aperture 100 of the blade 96. The snug fit of the boss 122 of the actuator block 120 in the aperture 100 prevents rotation of the actuator block relative to the blade 96. A blind hole 124 extends into the boss 122. The blind hole 124 is sized for receiving the locking pin of the actuator handle 108 to secure together the actuator handle, the blade 96, and the actuator block 120.

A first pair of skin grippers 130 is attached to the actuator block 120 by associated helical springs 132. The skin grippers 130 includes main body portions 134 that are received in the recess 38 of the base plate portion 14 of the housing 12. Each of the skin grippers 130 is adapted to slide relative to an associated elongated slot 40. Tines 136 extend from a lower surface of the main body portions of the skin grippers 130. When the skin grippers 130 are located in their associated elongated slots 40, the tines 136 extend downward below the lower surface 20 of the base plate portion 14 and are angled slightly toward the elliptical aperture 34 of the base plate portion, as shown in FIG. 4.

The apparatus 10 also includes an adhesive bandage 140 (FIG. 4). The adhesive bandage 140 may be any known adhesive bandage. The adhesive bandage 140 includes opposite first and second side surfaces 142 and 144, respectively. An adhesive of the adhesive bandage 140 is located on the first side surface 142 of the adhesive bandage.

The apparatus 10 also includes a device 150 for applying the adhesive bandage 140 to a patient's skin 154 (FIG. 4) for closing a wound 156 (FIG. 10) resulting from the excision of tissue. The device 150 includes a liner 160 that is made from a generally resilient material, such as siliconized paper. The liner 160 includes a central portion 162 that defines an elliptical opening 164 and first and second elongated end portions 166 and 168, respectively. A width of the first end portion 166 of the liner 160 is approximately equal to the width of the adhesive bandage 140. A terminal end of the second elongated end portion 168 is secured to an anchor pin 172. The anchor pin 172 is an elongated cylindrical rod that is sized for placement in the anchor pin slot 62 of the recess 50 of the base plate portion 14.

The device 150 also includes first and second roller members 174 and 176, respectively. The first roller member 174 is cylindrical and is sized for placement in the rectangular portion 52 of the recess 50. The first roller member 174 has a length that is approximately equal to the lateral extent of the rectangular portion 52 of the recess 50 so that, when received in the rectangular portion, the first roller member 174 is confined for movement only in the longitudinal direction. The second roller member 176 is also cylindrical and is sized for placement in the roller slot 64 of the recess 50. The diameter and length of the second roller member 176 are such that, when located in the roller slot 64, the second roller member 176 is confined against both lateral and longitudinal movement relative to the base plate portion 14. The second roller member 176 may rotate about its central axis when located in the roller slot 64 of the recess 50.

When the device 150 is assembled, the first end portion 166 of the liner 160 is located on the lower surface 20 of the base plate portion 14 between the skin grippers 130. A low strength adhesive secures the first end portion 166 of the liner 160 to the lower surface 20 of the base plate portion 14. The elliptical opening 164 of the central portion 162 of the liner 160 is aligned with the elliptical aperture 34 in the base plate portion 14 of the housing 12. The second end portion 168 of the liner 160 extends through the through-hole 66 and around the second roller member 176 located in the roller slot 64 of the recess 50. The second end portion 168 of the liner 160 then passes over the first roller member 174 that is located in the rectangular portion 52 of the recess 50, as shown in FIG. 4, and terminates at the anchor pin 172. The anchor pin 172 is located in the anchor slot 62 of the base plate portion 14 of the housing 12.

Another molded plastic actuator handle 182 is associated with the device 150. The actuator handle 182 includes an actuation surface 184 (FIG. 4) and a rectangular lower surface 186 (FIG. 1). First and second spaced apart lock members 188 extend downwardly from the lower surface 186. The first and second lock members 188 are adapted to lock onto the first roller member 174 on opposite sides of the liner 160. When the first and second lock members 188 are locked onto the first roller member 174, a gap, through which a portion of the liner 160 extends, is located between the first roller member 174 and the lower surface 186 of the actuator handle 182.

A second pair of skin grippers 194 is attached to the first and second lock members 188 associated with actuator handle 182 by associated helical springs 196. The skin grippers 194 include main body portions 198 that are received in the rectangular portion 52 of the recess 50 of the base plate portion 14 of the housing 12. Each of the skin grippers 194 is adapted to slide relative to an associated elongated slot 54. Tines 200 extend from a lower surface of the skin grippers 194. When the skin grippers 194 are located in their associated elongated slots 54, the tines 200 extend downward below the lower surface 20 of the base plate portion 14 and are angled slightly toward the elliptical aperture 34 of the base plate portion, as shown in FIG. 4.

According to one method of assembling the apparatus 10, the second end portion 168 of the liner 160 is inserted through the through-hole 66 and into the roller slot 64 of the recess 50 of the base plate portion 14. The anchor pin 172 is attached to the terminal end of the second end portion 168 of the liner 160. The second roller member 176 is positioned in the roller slot 64 of the recess 50 and the second end portion 168 of the liner 160 is pulled over the second roller member. Next, the second end portion 168 of the liner 160 is folded under itself and the first roller member 174 is positioned at the location of the fold. The anchor pin 172 is inserted into the anchor slot 62 of the base plate portion 14 and the first roller member 174 is positioned in the rectangular portion 52 of the recess 50 at a location nearest the anchor slot 62. When the first roller member 174 is positioned in the recess 50, the skin grippers 194 are inserted into their associated elongated slots 54 such that the tines 200 extend below the lower surface 20 of the base plate portion 14.

Next, the actuator block 120 is positioned in the recess 38 of the base plate portion 14 so that the skin grippers 130 are inserted into their associated elongated slots 40. When the skin grippers 130 are inserted into their associated elongated slots 40, the tines 136 of the skin grippers 130 extend below the lower surface 20 of the base plate portion 14. The blade 96 is then placed over the actuator block 120 so that the boss 122 of the actuator block extends through the aperture 100 of the blade. The top plate portion 16 is then placed atop the base plate portion 14 and fasteners 204 (FIG. 1) secure the top plate portion relative to the base plate portion.

After the top plate portion 16 is secured to the base plate portion 14, the actuator handle 108 is positioned over the exposed boss 122 of the actuator block 120 and the locking pin of the actuator handle 108 is inserted into the blind hole 124 of the boss of the actuator block. When the locking pin is received in the blind hole 124 of the boss 122, the actuator handle 108 is fixed for movement with the blade 96 and the actuator block 120.

Next, the actuator handle 182 is secured to the first roller member 174. To secure the actuator handle 182 to the first roller member 174, the actuator handle 182 is positioned over the first roller member 174 and is pressed downwardly so that the first and second lock members 188 snap onto the first roller member. When the first and second lock members 188 snap onto the first roller member 174, the second end portion 168 of the liner 160 extends through the gap located between the lower surface 186 of the actuator handle 182 and the first roller member 174 and also between the first and second locking members 188. When the actuator handle 182 is secured to the first roller member 174, the first roller member 174 is fixed for movement with the actuator handle 182.

The housing 12 of the apparatus 10 then is turned over and the first end portion 166 of the liner 160 is adhered, with a low strength adhesive, to the lower surface 20 of the base plate portion 14 to place the elliptical opening 164 of the liner in alignment with the elliptical apertures 34 and 78 of the base plate portion 14 and the top plate portion 16 of the housing 12. The adhesive bandage 140 is then folded longitudinally in half and a first half of the folded adhesive bandage 140 is adhered to the first end portion 166 of the liner 160 so that the fold of the adhesive bandage is located nearest the elliptical opening 164 of the liner, as shown in FIG. 4. A releasable paper backing (not shown) may be located on the second half of the adhesive bandage 140 until time for use of the apparatus 10.

To use the apparatus 10 for removing a portion of tissue 208 (FIG. 10), such as a skin lesion, the releasable paper backing is removed from the second half of the adhesive bandage 140. The lower surface 20 of the base plate portion 14 of the assembled apparatus 10 is placed against a patient's skin 154 so that the tissue to be excised is aligned with the elliptical apertures 34 and 78 of the housing 12. When the lower surface 20 of the base plate portion 14 is placed against the patient's skin 154, the second half of the adhesive bandage 140 adheres to the patient's skin 154. Also, when the lower surface 20 of the base plate portion 14 is placed against the patient's skin 154, the tines 136 and 200 of the skin grippers 130 and 194, respectively, protrude slightly into the skin for gripping the skin adjacent to the tissue to be removed. FIG. 4 schematically illustrates the tines 136 and 200 of the skin grippers 130 and 194 protruding into the skin 154.

A skin hook 212 (FIG. 4), or another device for grabbing tissue 208, is inserted through the elliptical apertures 34 and 78 of the housing 12. The skin hook 212 is manipulated for grabbing the tissue 208 and pulling the tissue through the elliptical apertures 34 and 78 of the housing 12. When pulled through the elliptical apertures 34 and 78, the tissue 208 is placed under tension.

The actuator handles 108 and 182 are pushed together for excising the tissue 208 and actuating the device 150 to apply the adhesive bandage 140. As shown with reference to FIGS.

3, 4, 6, and 7, when the actuator handles 108 and 182 are pushed together, the skin grippers 130 and 194 are moved toward the elliptical apertures 34 and 78. The tines 136 and 200 associated with skin grippers 130 and 194 secure the skin 154 adjacent the tissue 208 to be excised so that the skin hook 212 may tension the tissue.

Figure 3:
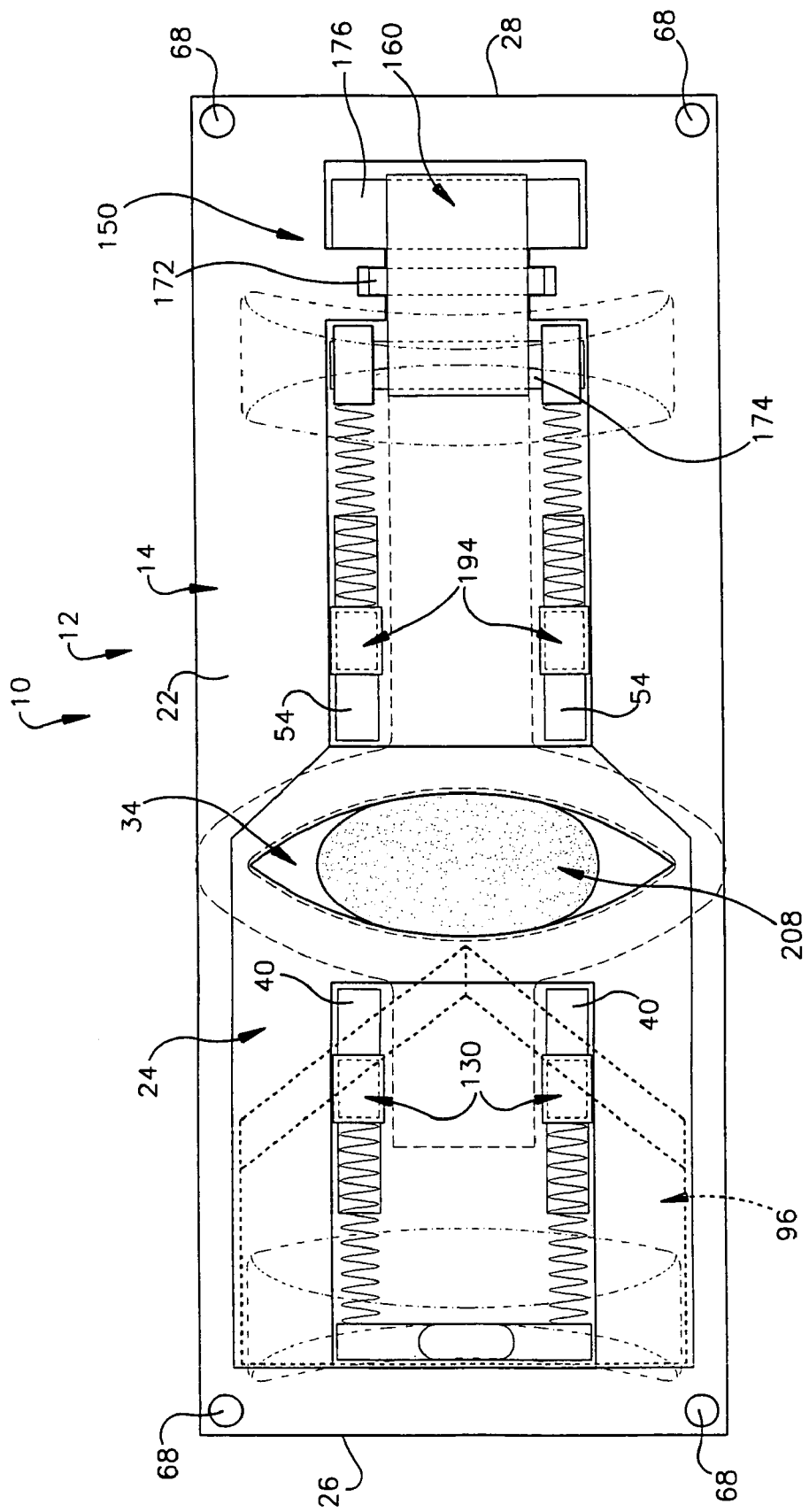
FIG. 3 is a plan view of the apparatus of FIG. 1 and illustrates a device in an initial position.
Figure 6:
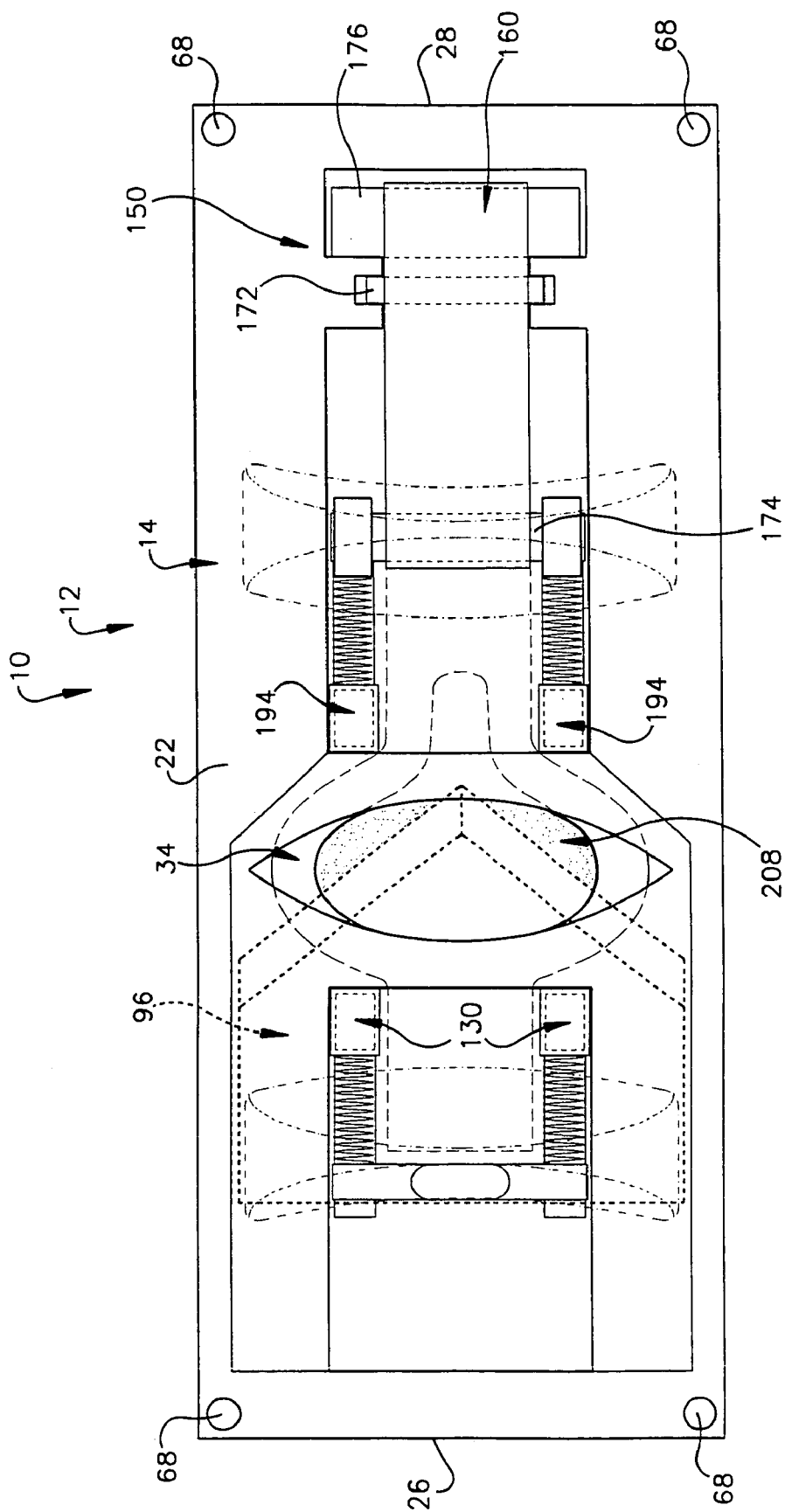
FIG. 6 is a plan view of the apparatus of FIG. 1 and illustrates the device in a partially actuated position.
Figure 9:
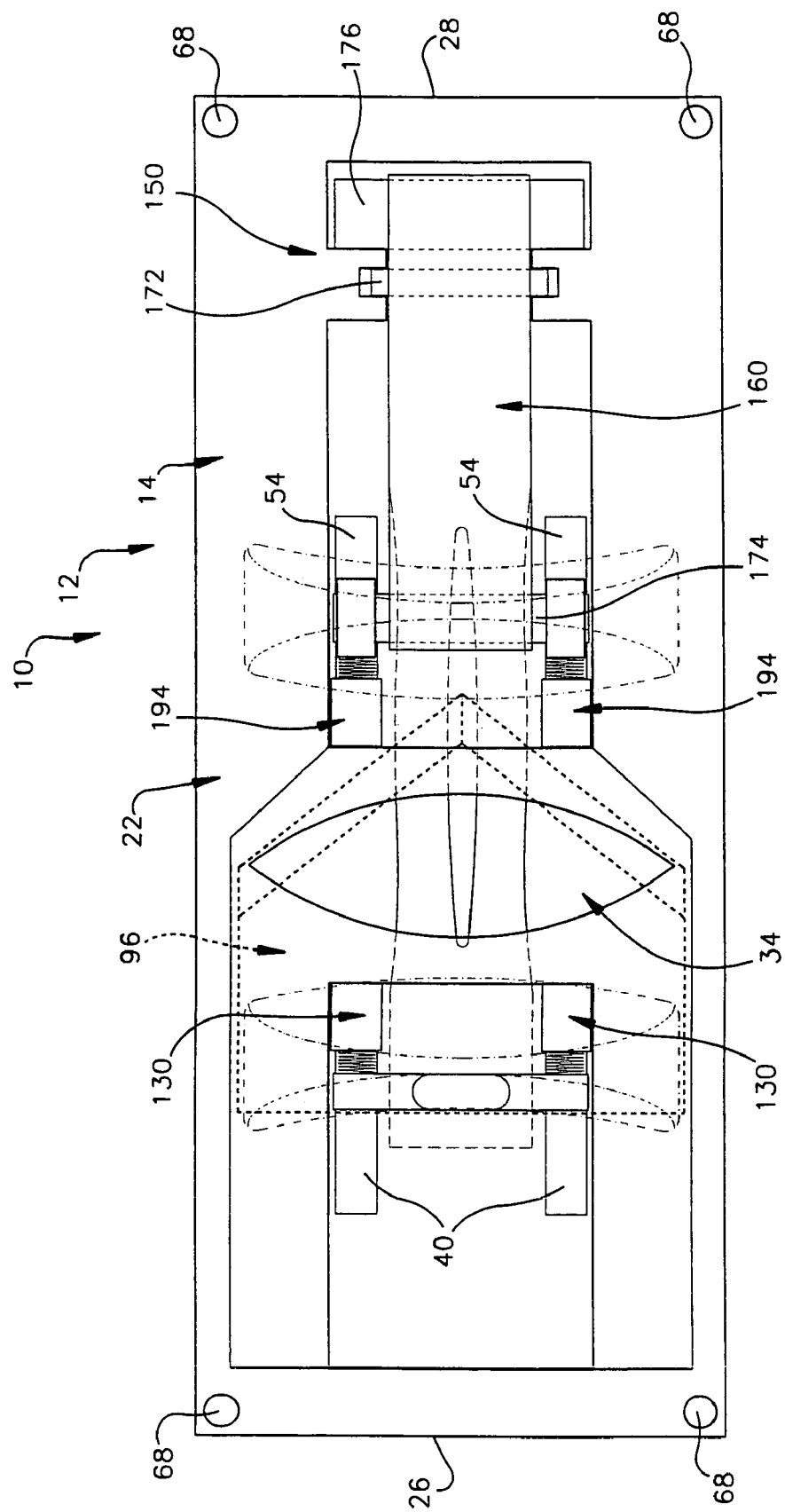
FIG. 9 is a plan view of the apparatus of FIG. 1 and illustrates the device in a fully actuated position.

As FIGS. 3 and 4 illustrate, the blade 96 is located immediately adjacent to the tissue 208 that is pulled through the elliptical apertures 34 and 78 prior to the actuator handle 108 being moved. When the actuator handle 108 is moved toward the elliptical apertures 34 and 78, the blade 96 begins to excise the tissue 208. FIG. 6 illustrates the blade 96 extending partially through the tissue 208. When the actuator handle 108 is moved into the position shown in FIGS. 9 and 10, the blade 96 extends completely through the tissue 208.

When the actuator handle 182 is moved toward the elliptical apertures 34 and 78, the device 150 for applying the adhesive bandage 140 is actuated. FIG. 4 illustrates the actuator handle 182 in its initial position. FIG. 5 illustrates the condition of the liner 160 when the actuator handle 182 is in the initial position. FIG. 5 also illustrates the position of liner 160 relative to the skin grippers 130 and 194. As FIG. 5 illustrates, when the actuator handle 182 is in the initial position, the tissue 208 extends through the elliptical opening 164 of the central portion 162 of the liner 160 and the liner is in a non-deformed condition.

When the actuator handle 182 is moved toward the elliptical apertures 34 and 78 of the housing 12, the first roller member 174 is moved with the actuator handle 182 in a direction away from the anchor pin 172. As the first roller member 174 moves away from the anchor pin 172, the second end portion 168 of the liner 160 is pulled around the first and second roller members 174 and 176. As a result, the amount of the second end portion 168 of the liner 160 located between the anchor pin 172 and the second roller member 176 increases. The increased amount of the second end portion 168 of the liner 160 that is located between the anchor pin 172 and the second roller member 176 is greater than 1:1 the amount of movement of the actuator handle 182 relative to the housing 12. In the embodiment illustrated, the increased amount of the second end portion 168 of the liner 160 that is located between the anchor pin 172 and the second roller member 176 is equal to twice the amount of movement of the actuator handle 182 relative to the housing 12.

Figure 7:
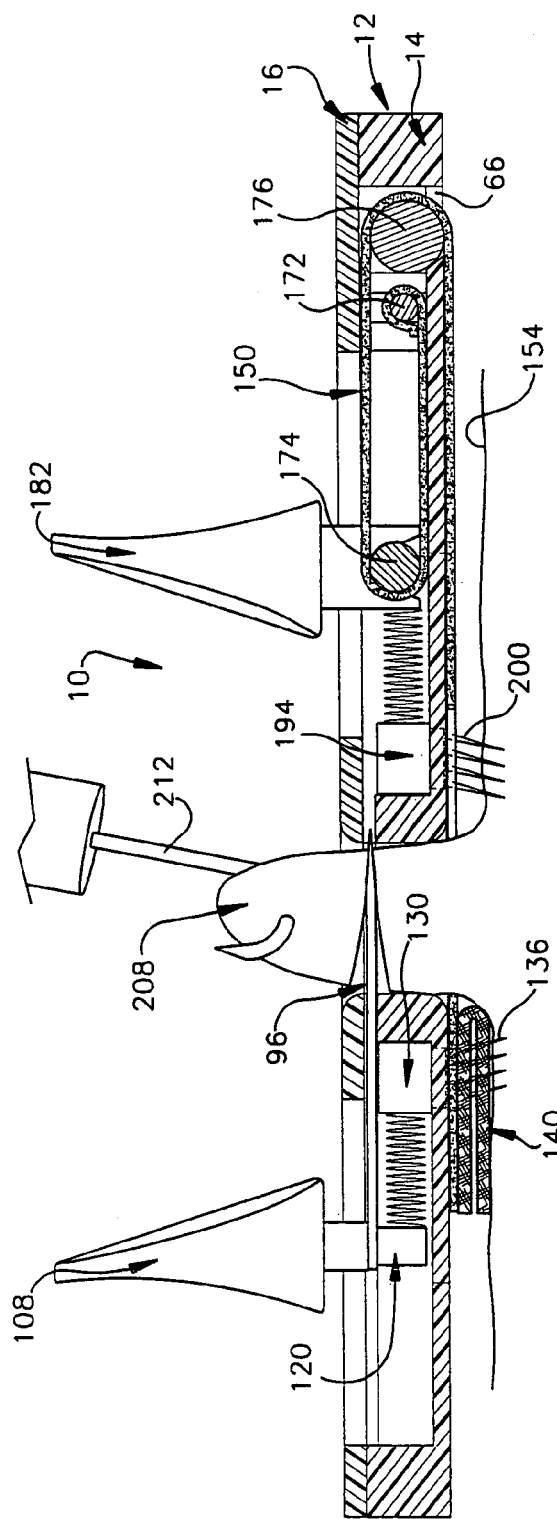
FIG. 7 is a sectional view of the apparatus of FIG. 1 and illustrates the device in the partially actuated position.
Figure 8:
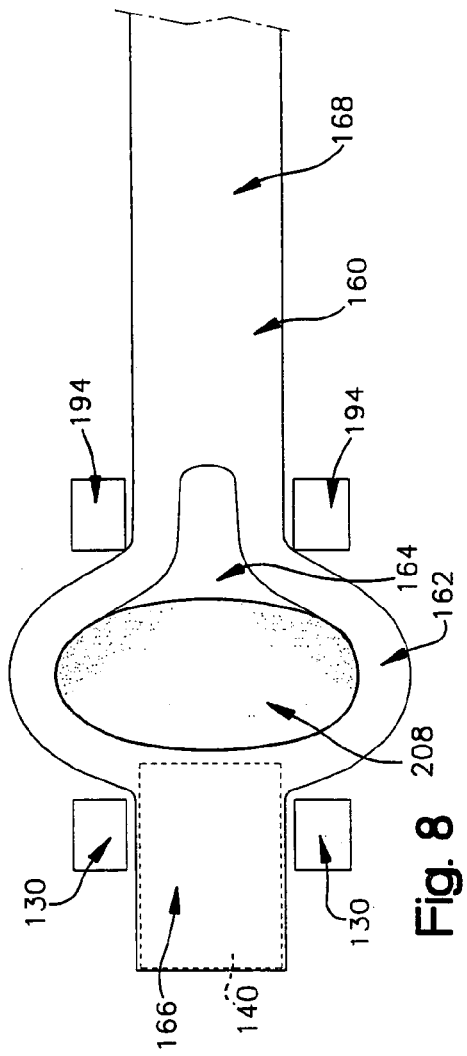
FIG. 8 schematically illustrates the condition of the liner when the device is in the partially actuated position.

As the second end portion 168 of the liner 160 is pulled about the first and second roller members 174 and 176, the elliptical opening 164 of the central portion 162 of the liner 160 is deformed into the condition illustrated in FIGS. 6-8. The part of the central portion 162 of the liner 160 located nearest the first end portion 166 abuts against the tissue 208 and is prevented from moving. The movement of the second end portion 168 of the liner 160 causes a deformation of the central portion 162 of the liner. Specifically, the elliptical opening 164 elongates into the condition illustrated in FIGS. 6 and 8.

A comparison of FIGS. 5 and 8 also shows that as the central portion 162 of the liner 160 is deformed, the skin grippers 130 and 194 move closer together. This movement of the skin grippers 130 and 194 helps to press together opposite sides of the wound 156 (FIG. 10) that results from the excision of the tissue 208.

Figure 10:
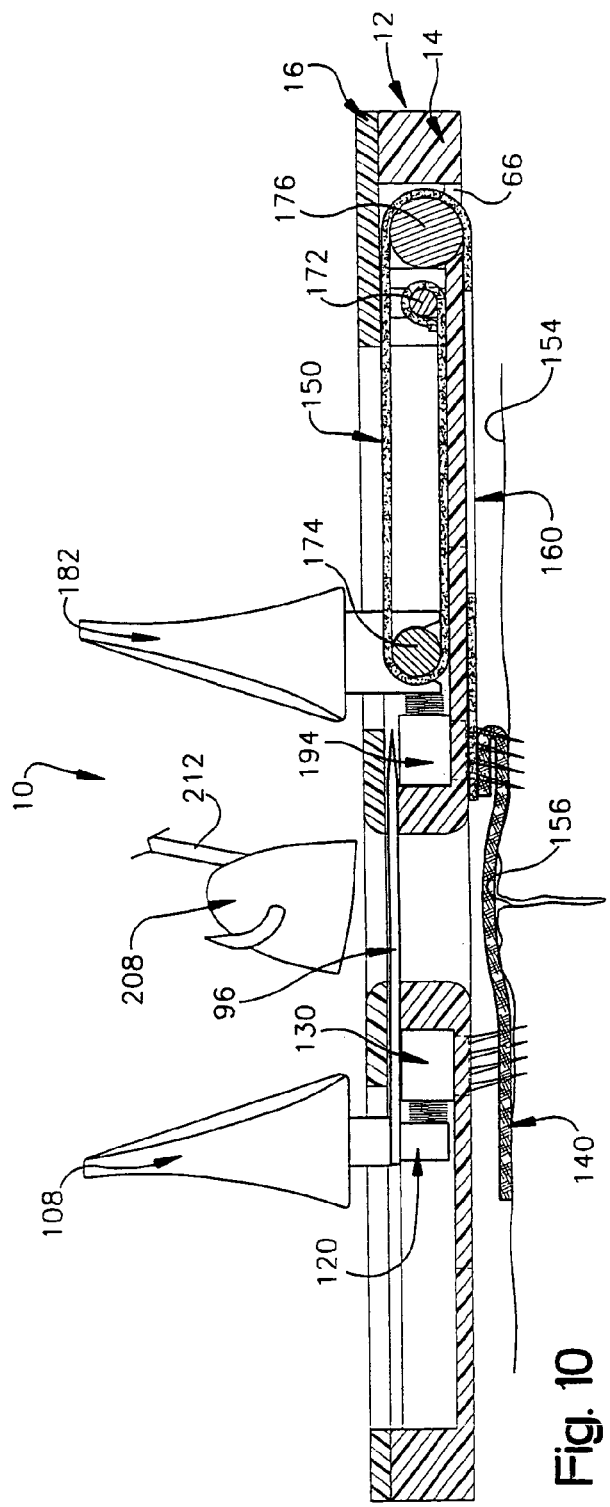
FIG. 10 is a sectional view of the apparatus of FIG. 1 and illustrates the device in the fully actuated position at a time immediately after the tissue is completely excised.
Figure 11:
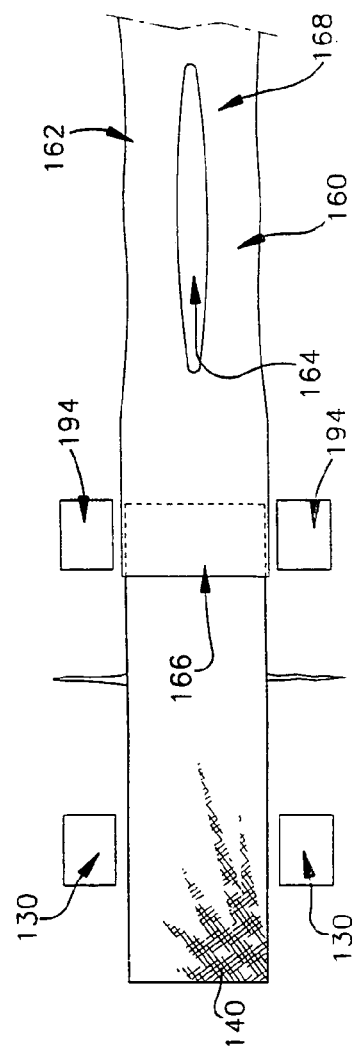
FIG. 11 schematically illustrates the condition of the liner when the device is in the fully actuated position and at a time immediately after the tissue is completely excised.

Further movement of the actuator handle 182 results in an additional amount of the second end portion 168 of the liner 160 moving into the housing 12 and being located between the second roller member 176 and the anchor pin 172. At the time the blade 96 completely excises the tissue 208, the edges of the resulting wound 156 pass through the elliptical opening 164 of the central portion 162 of the liner 160 to a location below the liner, as shown in FIG. 10. At the time immediately after the tissue 208 has been excised and the edges of the wound 156 have passed through the elliptical opening 164 of the central portion 162 of the liner 160, the elliptical opening 164 is deformed into the elongated condition illustrated in FIG. 11. When the central portion 162 is in the elongated condition illustrated in FIG. 11, the first end portion 166 of the liner 160 remains generally in its initial position.

Figure 12:
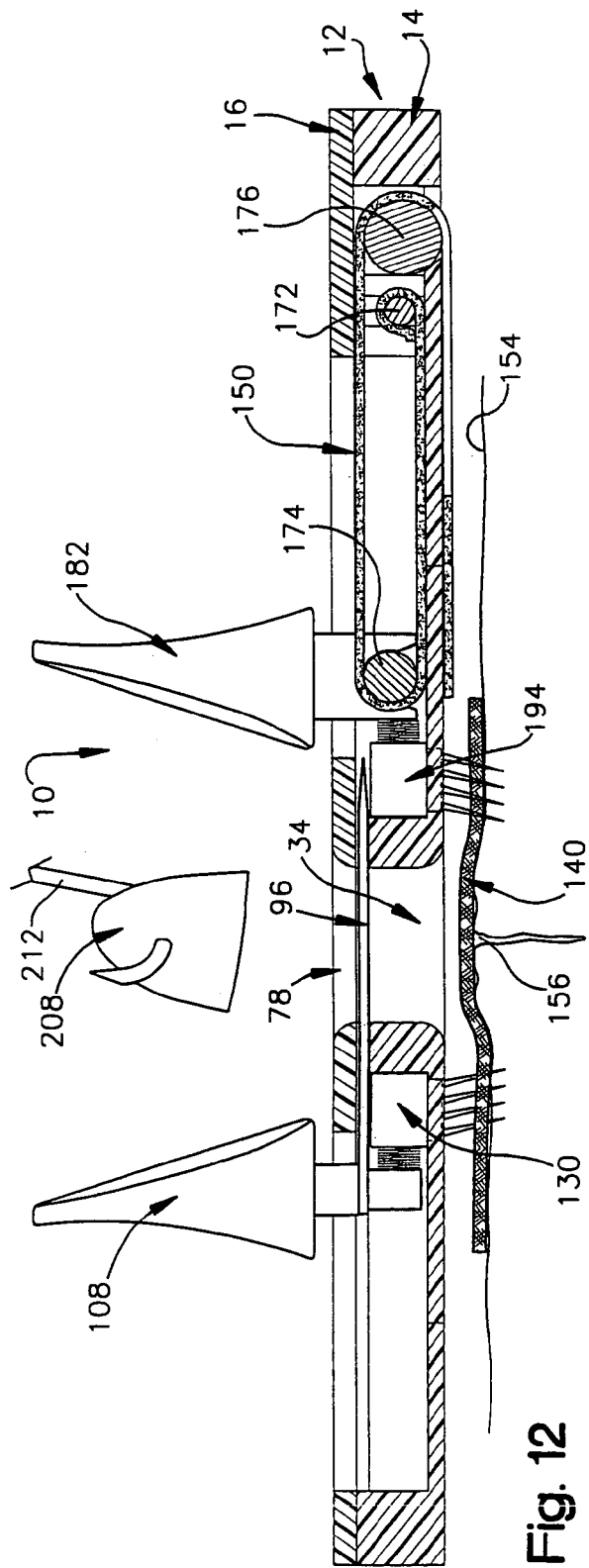
FIG. 12 is a sectional view of the apparatus of FIG. 1 and illustrates the device in the fully actuated position and at a time after the adhesive bandage has been applied to a resulting wound.
Figure 13:
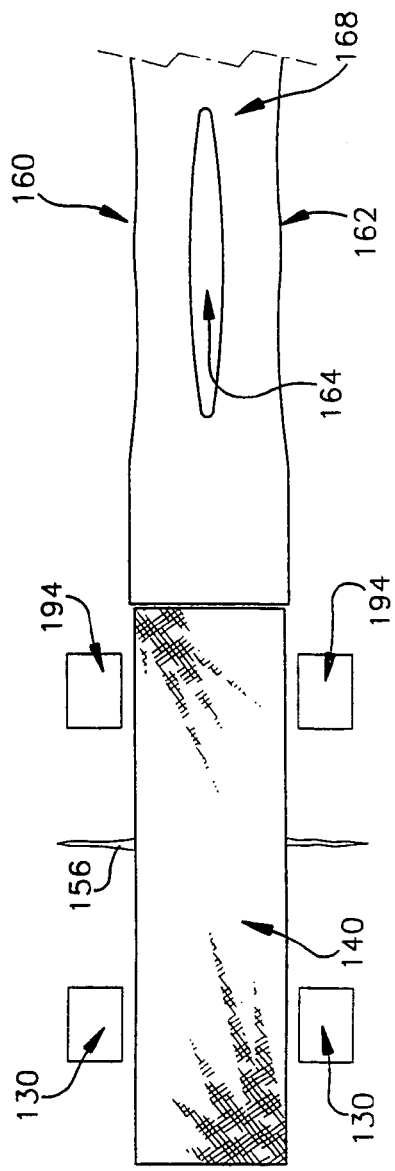
FIG. 13 schematically illustrates the condition of the liner when the device is in the fully actuated position and at a time after the adhesive bandage has been applied to the resulting wound.

Since the liner 160 is formed from an elastic material, the central portion 162 of the liner 160 has a tendency to return to its initial condition defining the elliptical opening 164. As the central portion 162 of the liner 160 begins to return to its initial condition, the first end portion 166 of the liner 160 is pulled rightward from the position shown in FIG. 11 to the position shown in FIG. 13. During the rightward movement of the first end portion 166 of the liner 160, the first half of the adhesive bandage 140 is pulled across the wound 156 and is adhered to the skin 154 on a side of the wound opposite the second half of the adhesive bandage. FIGS. 12 and 13 illustrate the adhesive bandage 140 extending over the wound 156 to close the wound.

After the adhesive bandage 140 closes the wound 156, the actuator handles 108 and 182 are released and the bias force of the springs 132 and 196 associated with the skin grippers 130 and 194 force the actuator handles apart. The apparatus 10 is then pulled away from the patient's skin 154 to remove the tines 136 and 200 of the skin grippers 130 and 194. The apparatus 10 of the present invention is a single use apparatus. Therefore, after the tines 136 and 200 of the skin grippers 130 and 194 are removed from the patient's skin 154, the apparatus 10 may be discarded.

Figure 14:
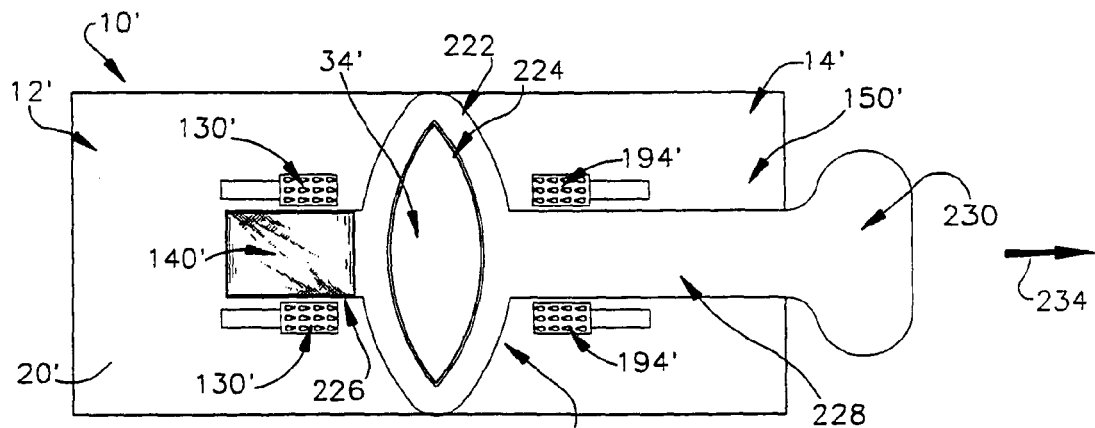
FIG. 14 is a bottom plan view of an apparatus constructed in accordance with a second embodiment of the present invention and illustrates a device for applying an adhesive bandage with the device in an initial condition.

FIG. 14 is a bottom plan view of an apparatus 10' constructed in accordance with a second embodiment of the present invention. The apparatus 10' of FIG. 14 is similar to the apparatus 10 described above with reference to FIGS. 1-13 with the exception of the device 150' for applying the adhesive bandage 140'. As such, the features of the apparatus 10' of FIG. 14 that are the same as or similar to those described with reference to FIGS. 1-13 have the same reference numbers with the addition of a prime. The features of the device 150' in FIG. 14 are labeled with new reference numbers.

In the apparatus 10' of FIG. 14, the device 150' for applying the adhesive bandage 140' includes only a liner 220. The liner 220 is made from a generally resilient material, such as siliconized paper. The liner 220 includes a central portion 222 that defines an elliptical opening 224 and first and second elongated end portions 226 and 228, respectively. A width of the first end portion 226 of the liner 220 is approximately equal to the width of the adhesive bandage 140'. A terminal end of the second end portion 228 includes an enlarged actuator portion 230. The actuator portion 230 is located outside of the footprint of the housing 12', as illustrated in FIG. 14.

The adhesive bandage 140' is folded longitudinally in half and a first half (not shown) of the folded adhesive bandage is adhered to the first end portion 226 of the liner 220 so that the fold of the adhesive bandage is located nearest the elliptical opening 224 of the liner. FIG. 14 illustrates the second half of the adhesive bandage 140'.

The first end portion 226 of the liner 220 and part of the second end portion 228 of the liner are adhered to the lower surface 20' of the base plate portion 14' of the housing 12' with a low strength adhesive. The low strength adhesive secures the liner 220 to the lower surface 20' of the base plate portion 14' so that the elliptical opening 224 of the liner aligns with the elliptical aperture 34' of the base plate portion of the housing, as shown in FIG. 14.

Figure 15:
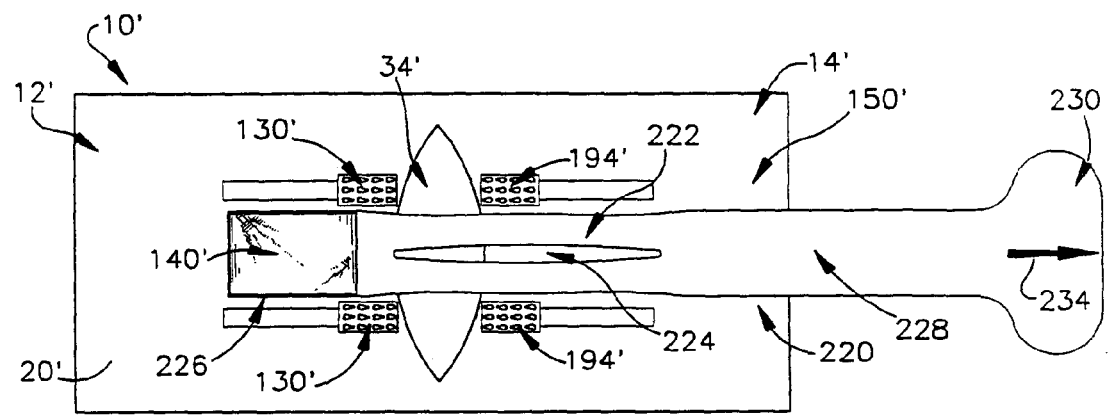
FIG. 15 illustrates the apparatus of FIG. 14 with the device in a partially actuated condition.

When the apparatus 10' of FIG. 14 is positioned on a patient's skin (not shown), the second half of the adhesive bandage 140' adheres to the skin. When the actuator handles (not shown) of the apparatus 10' are pushed together, the skin grippers 130' and 194' move together to help tension the tissue that is pulled through the elliptical aperture 34'. FIG. 14 illustrates the position of the skin grippers 130' and 194' prior to the actuator handles being pushed together and FIG. 15 illustrates the position of the skin grippers 130' and 194' after the actuator handles have been pushed together. Also, when the actuator handles are pushed together, the blade (not shown) excises the tissue extending through the elliptical aperture 34' and the skin grippers 130' and 194' help to push together opposite edges of the resulting wound.

The device 150' for applying the adhesive bandage 140' to close the resulting wound is actuated after the blade has excised the tissue. To actuate the device 150', the actuator portion 230 of the second end portion 228 of the liner 220 is grasped and is pulled in a direction away from the housing 12', i.e., in the direction of arrow 234 in FIG. 14. When the actuator portion 230 of the liner 220 is pulled away from the housing 12', the central portion 222 of the liner 220 deforms so that the elliptical opening 224 elongates, as shown in FIG. 15. Further movement of the actuator portion 230 of the liner 220 away from the housing 12' pulls the first end portion 226 of the liner 220 over the resulting wound. Movement of the first end portion 226 of the liner 220 over the resulting wound adheres the first half of the adhesive bandage 140' to the patient's skin on a side of the wound opposite the second half of the adhesive bandage. As a result, the wound is closed with the adhesive bandage 140'.

Figure 16:
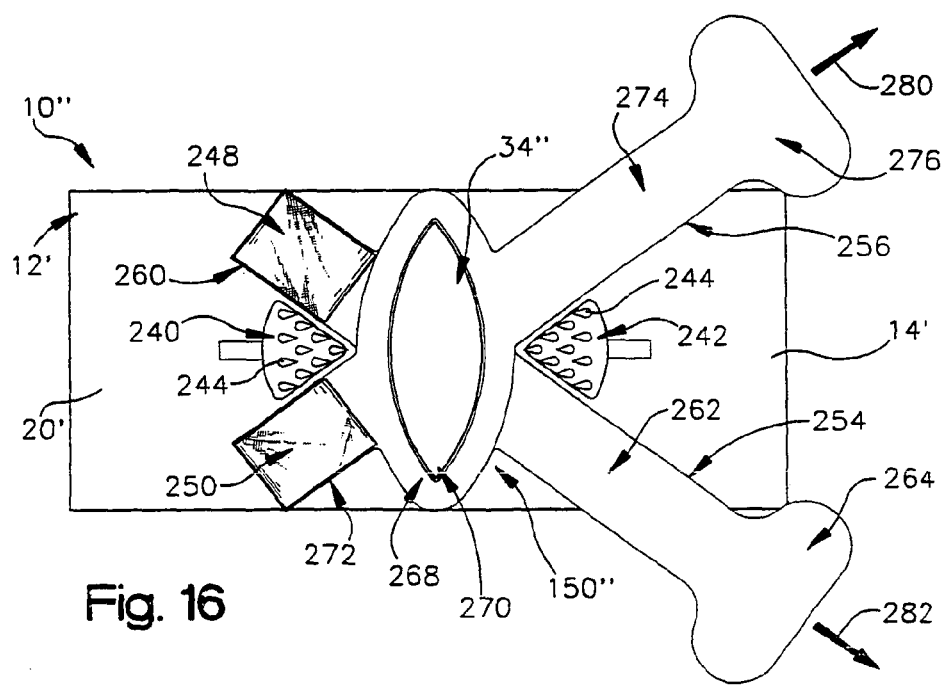
FIG. 16 is a bottom plan view of an apparatus constructed in accordance with a third embodiment of the present invention and illustrates a device for applying two adhesive bandages with the device in an initial condition.

FIG. 16 is a bottom plan view of an apparatus 10" constructed in accordance with a third embodiment of the present invention. With the exception of the skin grippers 240 and 242 and the device 150", the apparatus 10" of FIG. 16 is similar to the apparatus 10' described above with reference to FIG. 14. As a result, the features of the apparatus 10" of FIG. 16 that are the same as or similar to those described with reference to FIG. 14 have the same reference numbers with the addition of a second prime. The features of the skin grippers 240 and 242 and the device 150" are labeled with new reference numbers.

In the apparatus 10" of FIG. 16, a single skin gripper 240 or 242 is associated with each actuator handle (not shown). The skin grippers 240 and 242 have generally triangular shapes and are centered relative to the elliptical aperture 34" of the base plate portion 14" of the housing 12". Tines 244 extend below a lower surface of the skin grippers 240 and 242. Like the skin grippers 130' and 194' of FIG. 14, the skin grippers 240 and 242 of FIG. 16 move toward the elliptical aperture 34" when the actuator handles are pushed together.

The device 150" of the apparatus 10" of FIG. 16 applies two adhesive bandages 248 and 250 over the wound that results from the excision of the tissue. The device 150" includes first and second liners 254 and 256, respectively, each of which is made from a generally resilient material. The first liner 254 includes a central portion (not shown) that defines an elliptical opening and first and second elongated end portions 260 and 262, respectively. The elliptical opening is angled at approximately forty-five degrees relative to the extents of the first and second end portions 260 and 262. A width of the first end portion 260 of the first liner 254 is approximately equal to the width of a first adhesive bandage 248. A terminal end of the second end portion 262 includes an enlarged actuator portion 264. The actuator portion 264 is located slightly outside of and adjacent to a corner of the base plate portion 14" of the housing 12".

The first adhesive bandage 248 is folded longitudinally in half and a first half (not shown) of the folded first adhesive bandage is adhered to the first end portion 260 of the first liner 254 so that the fold of the first adhesive bandage is located nearest the elliptical opening of the first liner. FIG. 16 illustrates the second half of the first adhesive bandage 248.

The first end portion 260 of the first liner 254 and part of the second end portion 262 of the first liner are adhered to the lower surface 20" of the base plate portion 14" of the housing 12" with a low strength adhesive. The low strength adhesive secures the first liner 254 to the lower surface 20" of the base plate portion 14" so that the elliptical opening of the first liner aligns with the elliptical aperture 34" of the base plate portion 14" of the housing 12", as shown in FIG. 16.

The second liner 256 includes a central portion 268 that defines an elliptical opening 270 and first and second elongated end portions 272 and 274, respectively. As FIG. 16 illustrates, the elliptical opening 270 is angled at approximately forty-five degrees relative to the extents of the first and second end portions 272 and 274. A width of the first end portion 272 of the second liner 256 is approximately equal to the width of a second adhesive bandage 250. A terminal end of the second end portion 274 includes an enlarged actuator portion 276. The actuator portion 276 is located slightly outside of and adjacent to a corner of the base plate portion 14" of the housing 12".

The second adhesive bandage 250 is folded longitudinally in half and a first half (not shown) of the folded second adhesive bandage is adhered to the first end portion 272 of the second liner 256 so that the fold of the second adhesive bandage is located nearest the elliptical opening 270 of the second liner. FIG. 16 illustrates the second half of the second adhesive bandage 250.

The first end portion 272 of the second liner 256 and part of the second end portion 274 of the second liner are adhered to the lower surface 20" of the base plate portion 14" of the housing 12" with a low strength adhesive. The low strength adhesive secures the second liner 256 to the lower surface 20" of the base plate portion 14" so that the elliptical opening 270 of the second liner aligns with the elliptical aperture 34" of the base plate portion 14" of the housing 12" and the elliptical opening of the first liner 254.

When the apparatus 10" of FIG. 16 is positioned on a patient's skin, the second half of the first and second adhesive bandages 248 and 250 adhere to the skin. When the actuator handles (not shown) of the apparatus 10" are pushed together, the skin grippers 240 and 242 move together to help tension the tissue that is pulled through the elliptical aperture 34". Also, when the actuator handles are pushed together, the blade (not shown) excises the tissue extending through the elliptical aperture 34" and, the skin grippers 240 and 242 help to push together opposite edges of the resulting wound.

The device 150" to close the resulting wound is actuated after the blade has excised the tissue. To actuate the device 150", the actuator portion 276 of the second end portion 274 of the second liner 256 is grasped and is pulled in a direction away from the corner of the housing 12", i.e., in the direction of arrow 280 in FIG. 16. When the actuator portion 276 of the second liner 256 is pulled away from the housing 12", the central portion 268 of the second liner 256 deforms so that the elliptical opening 270 elongates. Further movement of the actuator portion 276 of the second liner 256 away from the housing 12" pulls the first end portion 260 of the second liner over the resulting wound. Movement of the first end portion 260 of the second liner 256 over the resulting wound adheres the first half of the second adhesive bandage 250 to the patient's skin on a side of the wound opposite the second half of the second adhesive bandage. As a result, the wound is closed with the second adhesive bandage 250.

Next, the actuator portion 264 of the second end portion 262 of the first liner 254 is grasped and is pulled in a direction away from the corner of the housing 12", i.e., in the direction of arrow 282 in FIG. 16. When the actuator portion 264 of the first liner 254 is pulled away from the housing 12", the central portion of the first liner 254 deforms so that the elliptical opening elongates. Further movement of the actuator portion 264 of the first liner 254 pulls the first end portion 260 of the first liner 254 over the resulting wound. Movement of the first end portion of the first liner over the resulting wound adheres the first half of the first adhesive bandage 248 to the patient's skin on a side of the wound opposite the second half of the first adhesive bandage. As a result, first adhesive bandage 248 crosses the second adhesive bandage 250 and, both the first and second adhesive bandages 248 and 250 close the wound.

From the above description of the invention, those skilled in the art will perceive improvements, changes and modifications. Such improvements, changes and modifications within the skill of the art are intended to be covered by the appended claims.

Having described the invention, we claim the following:

1. An apparatus for excising tissue and closing a wound that results from excision of the tissue, the apparatus comprising:
    a structure defining an aperture into which tissue to be excised is exposed;
    a cutting member;
    an adhesive bandage strip for mechanically closing the wound, the adhesive bandage strip secured relative to a lower surface of the structure in a location for contacting skin adjacent to the tissue to be excised;
    a device actuatable for closing the wound with the adhesive bandage strip; and
    actuators for moving the cutting member relative to the structure for excising the tissue exposed in the aperture and for actuating the device.

2. The apparatus of claim 1 wherein the device includes a liner to which a portion of the adhesive bandage strip is attached, actuation of the device moving the liner relative to the lower surface of the structure to close the wound with the adhesive bandage strip.

3. The apparatus of claim 2 wherein, prior to actuation of the device, the liner lies adjacent to the lower surface of the structure, the adhesive bandage strip being secured to the liner.

4. The apparatus of claim 3 wherein the liner includes an opening and the aperture of the structure is elliptical, the opening of the liner aligning with the aperture of the structure when the liner is secured relative to the lower surface of the structure.

5. The apparatus of claim 4 wherein the liner is formed from a resilient material, the elliptical opening deforming during actuation of the device.

6. The apparatus of claim 2 wherein the device further includes at least one roller member over which the liner is moved during actuation.

7. The apparatus of claim 2 wherein the device is configured to move the liner over a distance greater than a distance traveled by the actuator for actuating the device.

8. The apparatus of claim 6 wherein the device includes two roller members over which the liner is moved during actuation, the liner moving over a distance greater than 1:1 of a distance traveled by the actuator for actuating the device.

9. The apparatus of claim 2 wherein the actuator for actuating the device is formed at an end of the liner.

10. The apparatus of claim 9 wherein, to actuate the device, the actuator for actuating the device is manually grasped and is pulled in a direction away from the structure.

11. The apparatus of claim 2 wherein the liner is a first liner and the device also includes a second liner for closing the wound, the adhesive bandage strip being a first adhesive bandage strip and being associated with the first liner for closing the wound, a second adhesive bandage strip for closing the wound being associated with the second liner, actuation of the device closing the wound with the first and second adhesive bandage strips.

12. The apparatus of claim 1 further including skin grippers associated with the actuators and including tines for gripping the skin adjacent the tissue to be excised.

13. The apparatus of claim 12 wherein the tines secure the skin adjacent to the tissue to be excised for enabling the tissue to be excised to be tensioned.

14. The apparatus of claim 12 wherein the tines move together for pressing together opposite edges of the wound prior to the adhesive bandage strip closing the wound.

* * * * *